United States Patent [19]

Kosugi et al.

[11] 4,338,945
[45] Jul. 13, 1982

[54] METHOD AND RANDOMIZED ELECTRICAL STIMULATION SYSTEM FOR PAIN RELIEF

[75] Inventors: Yukio Kosugi; Jun Ikebe; Kintomo Takakura; Yoriaki Kumagai, all of Tokyo, Japan

[73] Assignee: Clinical Engineering Laboratory Limited, Tokyo, Japan

[21] Appl. No.: 17,013

[22] Filed: Mar. 2, 1979

[30] Foreign Application Priority Data

Mar. 3, 1978 [JP] Japan .................................. 53-24346

[51] Int. Cl.³ ............................................... A61N 1/36
[52] U.S. Cl. ................................................ 128/421
[58] Field of Search ........... 128/419 R, 420 A, 420 R, 128/421, 422, 423 R, 423 W, 1 C; 331/78

[56] References Cited

U.S. PATENT DOCUMENTS

| | | | |
|---|---|---|---|
| 2,350,797 | 6/1944 | Morland et al. | 128/421 |
| 3,489,152 | 1/1970 | Barbara | 128/422 |
| 3,650,277 | 3/1972 | Sjostrand et al. | 128/421 |
| 3,822,708 | 7/1974 | Zilber | 128/419 R |
| 3,911,930 | 10/1975 | Hagfurs et al. | 128/421 |
| 3,983,881 | 10/1976 | Wickham | 128/422 |
| 4,062,365 | 12/1977 | Kameny | 128/422 |
| 4,153,059 | 5/1979 | Fravel | 128/422 |

OTHER PUBLICATIONS

Takakura et al., "Applied Neurophysiology", Basel, Switzerland, 1979, vol. 42, pp. 314–315.

*Primary Examiner*—William E. Kamm
*Attorney, Agent, or Firm*—Martin A. Farber

[57] ABSTRACT

System for generating electrical pulses for relieving the pain of the patient comprising a pulse generator and a controller for modulating the parameters of the output pulses of the pulse generator to fluctuate in accordance with the 1/f rule; i.e. the spectral density of the fluctuation varies inversely with the frequency.

7 Claims, 9 Drawing Figures

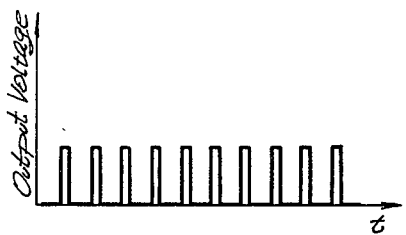
FIG. 1
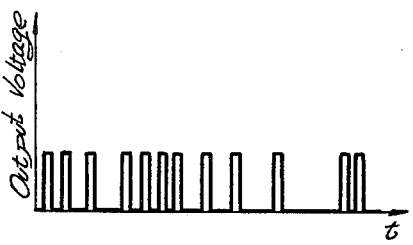
FIG. 2
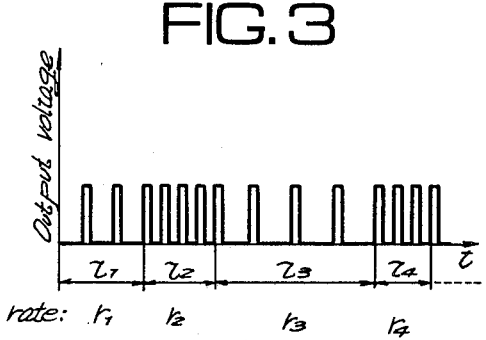
FIG. 3
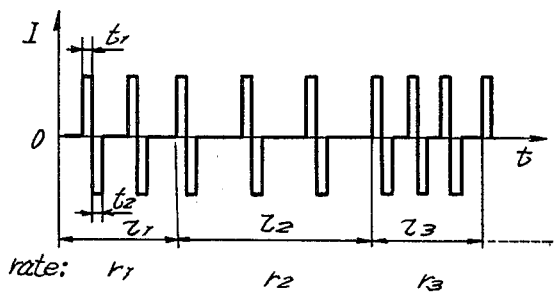
FIG. 7
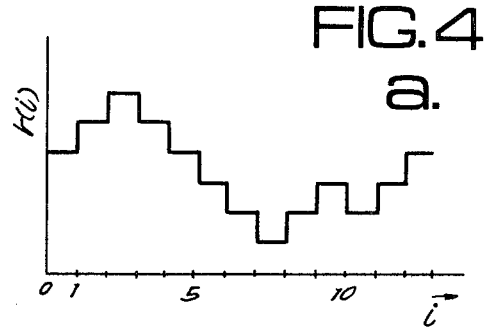
FIG. 4 a.
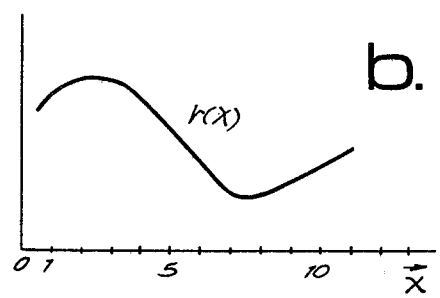
b.
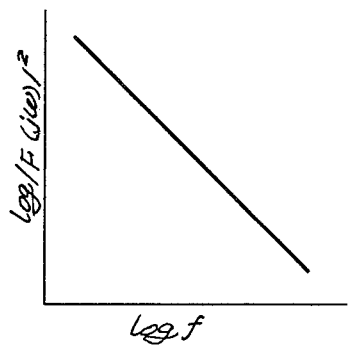
c.

METHOD AND RANDOMIZED ELECTRICAL STIMULATION SYSTEM FOR PAIN RELIEF

BACKGROUND OF THE INVENTION

This invention relates to a method for pain relief and to electrical stimulation systems for generating random pulse trains to be used for pain relief.

The existence of inhibitory neurons in the pain-transmitting nervous system in mammalian bodies is well known. Percutaneous electrical stimulations of dorsal column and/or peripheral nerves sometimes successfully produce selective excitation of inhibitory neurons in substantial gelatinosa or other ganglia in the central nervous system, resulting in temporal abolition of pain.

A typical pulse train conventionally used for the stimulation is depicted in FIG. 1, in which stimulation parameters such as pulse rate, pulse width and pulse amplitude do not change in time course. After a long-time use of such a stimulation which adopts uniform or simple periodic stimuli, the nervous system reveals adaptation effect against the stimuli. The monotony of the pattern is thought to be one of the reasons that the pain suppression effect diminishes in the long course of time.

For this reason, the stimulation pattern should be more variable and possibly be more comfortable.

The object of this invention is to provide a system which may produce a irregular stimulation by modulating pulses with random signals to give fresh sensations to the nervous system ceaselessly.

BRIEF DESCRIPTION OF THE DRAWINGS

FIG. 1 shows a pulse train conventionally used in electrical pulse stimulations, FIG. 2 shows a pulse train of an example of the present invention, FIG. 3 shows a pulse train of another example of the present invention, FIGS. 4a to 4c are graphs showing the 1/f rule interpreted in the stimulation respectively, FIG. 7 shows output pulses from the system of FIG. 6.

PREFERRED EMBODIMENTS OF THE INVENTION

An example of the irregular pulse train adopted in this invention is shown in FIG. 2. Note that the pulse intervals changes at random.

The second point of this invention is that the sequence of pulses has a moderate irregularity in order to ensure the comfortable sensation of the patient during the stimulation. An example of the moderately-irregular pulse train is shown in FIG. 3. Pulses are generated at a rate r1 during the period $\tau 1$, then at r2 during $\tau 2$ and so on, where rate sequence (r1, r2, r3 . . . ) and duration sequence ($\tau 1, \tau 2, \tau 3$ . . . ) are stochastically characterized by so called "1/f fluctuation rule" respectively. "1/f fluctuation" is defined as those fluctuation whose spectral density varies inversely with frequency. In this case, the rule may be interpreted as follows: When the rate sequence r(i) (i=1, 2, 3 . . . ) is plotted in order, it would be something like what is shown in FIG. 4a, and further apply smoothing as shown in FIG. 4b, then the Fourier transform $F(j\omega)$ of r(x) will give a power spectrum $|F(j\omega)|^2$ as shown in FIG. 4c where $\omega = 2\pi f$ and the plot is in logarithmic scales. The same interpretation is done on the duration sequence $\tau(i)$ (i=1, 2, 3 . . . ).

Figure 5:
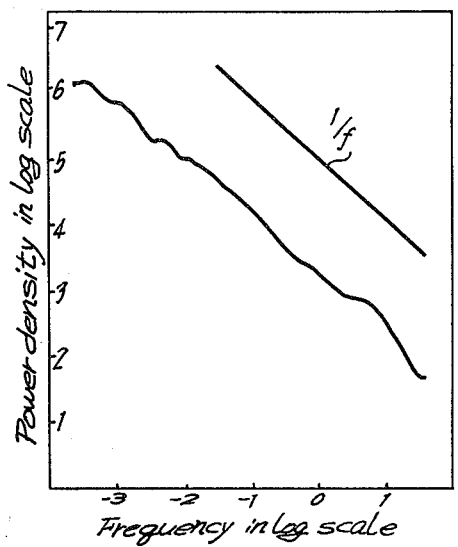
FIG. 5 shows power spectrum of the frequency-fluctuation of classical music.

It is known that pleasant stimuli, such as good music, to sensory organs often involve the stochastic fluctuation governed by 1/f. For example, the frequency fluctuation of so-called good classical music has this tendency over a frequency range of several decades as shown in FIG. 5.

As mentioned above, the moderately-irregular stimulation gives an adequately-fresh and not-so-abrupt a sensation to patients suffering from pain, when the 1/f rule is applied to the pulse-rate sequence and the sequence of durations within which the pulse rate is constant.

Ideally the 1/f tendency should last down to infinitely low frequencies. However, in the practical use, the very low frequency component can be disregarded, so that the 1/f fluctuation can be approximated by a "quasi 1/f" signal which has a periodicity of sufficient length.

(EXAMPLE I)

Figure 6:
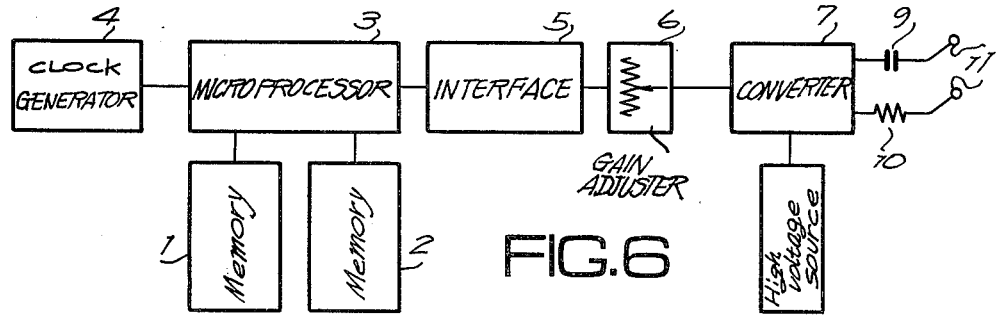
FIG. 6 shows a system block diagram of the first embodiment of the present invention.

The first example of the 1/f-fluctuated-stimulation system is schematically shown in FIG. 6. A pair of 1/f-fluctuation sequences are extracted from the long period frequency-changes of classical musics (eg. Beethoven's "Emperor" and Vivaldi's violin concerto). One sequence is used to assign the pulse rates into 8 levels over 10–100 pps and the other one is for the duration assignment to 4 levels over 0.5–4 seconds. The blocks 1 and 2 are memories which contain the pulse rate sequence and the duration sequence respectively. The microprocessor 3 processes the contents of these memories and generates the 1/f fluctuated pulses with the aid of the clock generator 4. The waveform of each pulse consists of a preceding positive pulse of 100 $\mu$sec-width and the subsequent negative pulse of the same width. A train of the compound pulses, shown in FIG. 7, is applied, via interface 5 and gain adjuster 6, to the voltage-to-current converter 7 with a high voltage source 8, then applied to the stimulation electrodes 11, where a capacitor 9 and a resistor 10 are provided to protect the patients in an emergency. In the above example, the periodicity of the stimulation pattern is restricted by the memory size.

(EXAMPLE II)

Figure 8:
FIG. 8 is a block diagram of 1/f generator.
Figure 9:
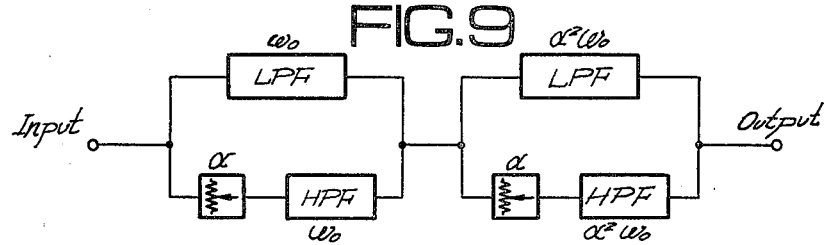
FIG. 9 shows an equivalent circuitry of the 1/f-filter.

The second example of the system is similar to that of the example I, except that the memories 1 and 2 in FIG. 6 are replaced by the 1/f fluctuation generator depicted in FIG. 8. The 1/f generation is, in this case, carried out in a microprocessor with software of a quasi-random generator and a 1/f digital filter. The equivalent circuitry of the 1/f digital filter consists of two low pass filters of the first order CR type with the cutoff frequencies $\omega o$ and $\alpha^2 \omega$., two high pass filters of the order CR type with cutoff frequencies $\omega o$ and $\alpha^2 \omega o$ and two attenuators with gain $\alpha (\simeq \frac{1}{4})$ as shown in FIG. 9 schematically. In this example, the 1/f fluctuation can be obtained over three decades of the frequency range without using large size memories.

What is claimed is:

1. An electrical pulse generation system to be used for the stimulation of dorsal column and peripheral nerves, respectively, for pain relief comprising
    a pulse generator,
    means having output electrodes constituting means adapted to be applied to central and peripheral nerve areas of a patient for automatically continuously randomizing parameters of output pulses of said pulse generator to generate a series of pulses having a specified power spectrum so as to ceaselessly provide fresh sensations to a nervous system through said electrodes.

2. The electrical pulse generation system as set forth in claim 1, wherein
    the series of pulses have a 1/f power spectrum.

3. The electrical pulse generation system as set forth in claim 1, wherein
    said controller means comprises a quasi-random generator and a 1/f filter for generating said series of pulses with a 1/f power spectrum so as to ceaselessly provide the fresh sensations to the nervous system.

4. An electrical pulse generation system to be used for the stimulation of dorsal column and peripheral nerves, respectively, for pain relief comprising
    a pulse generator,
    means having output electrodes constituting means adapted to be applied to central and peripheral nerve areas of a patient for generating a series of pulses of the pulse generator to fluctuate in accordance with the 1/f rule wherein the spectral density of the fluctuation varies inversely with the frequency.

5. An electrical pulse generation system to be used for the stimulation of dorsal column and peripheral nerves, respectively, for pain relief comprising
    a pulse generator,
    means for providing output pulses of the pulse generator with a sequence of durations, within which the pulse rate is constant, to fluctuate in accordance with the 1/f rule wherein the spectral density of the fluctuation varies inversely with the frequency,
    said means having electrode means for applying said sequence of durations to a patient for applying said stimulation of the dorsal column and peripheral nerves.

6. A method for pain relief by stimulation of the dorsal column and peripheral nerves, comprising the steps of
    generating continuously randomized parameters comprising a series of pulses having a specified power spectrum so as to ceaselessly provide fresh sensations to a nervous system,
    applying said series of pulses to the dorsal column and peripheral nerves.

7. The method as set forth in claim 6, wherein
    the series of pulses fluctuate in accordance with the 1/f rule wherein the spectral density of the fluctuation varies inversely with the frequency.

* * * * *